United States Patent
Sas et al.

(10) Patent No.: US 7,125,854 B2
(45) Date of Patent: *Oct. 24, 2006

(54) BICYCLIC CARBOHYDRATES AS ANTIPROTOZOAL BIOACTIVE FOR THE TREATMENT OF INFECTIONS CAUSED BY PARASITES

(75) Inventors: Benedikt Sas, Stekene (BE); Johan Van hemel, Antwerp (BE); Jan Vandenkerckhove, Zichem (BE); Eric Peys, Balen (BE); Johan Van der Eycken, Ninove (BE); Bart Ruttens, Ghent (BE)

(73) Assignee: Kemin Pharma B.V.B.A., Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/752,792

(22) Filed: Jan. 7, 2004

(65) Prior Publication Data

US 2004/0180838 A1    Sep. 16, 2004

Related U.S. Application Data

(60) Provisional application No. 60/438,474, filed on Jan. 7, 2003.

(51) Int. Cl.
*A01N 43/04* (2006.01)
*A01N 43/16* (2006.01)
*A61K 31/70* (2006.01)
*A61K 31/35* (2006.01)

(52) U.S. Cl. .......................... 514/23; 514/25; 549/364; 549/365

(58) Field of Classification Search ................. 514/25; 544/7, 14, 89, 127; 549/23, 364
See application file for complete search history.

(56) References Cited

U.S. PATENT DOCUMENTS

| 5,137,578 | A | 8/1992 | Chan |
| 5,147,463 | A | 9/1992 | Eilerman et al. |
| 6,242,484 | B1* | 6/2001 | Ojo-Amaize et al. ....... 514/475 |
| 2003/0158243 | A1* | 8/2003 | Sas et al. ................ 514/375 |
| 2004/0209823 | A1* | 10/2004 | Sas et al. ................ 514/23 |
| 2005/0059612 | A1* | 3/2005 | Sas et al. ................ 514/23 |
| 2005/0267048 | A9* | 12/2005 | Sas et al. ................ 514/25 |

FOREIGN PATENT DOCUMENTS

WO    WO 03/082846 A1    10/2003
WO    WO 01/014929 A1    2/2004

OTHER PUBLICATIONS

Murphy et al. Sterospecific Synthesis of B-D-allopyranosides by dihydroxylation of B-D-erythro-2,3-dideoxyhex-2-enopyranosides. 2001. Carbohydrate Research 334 (2001) pp. 327-335.*
Yoshida et al. Synthesis of a Set of di- and tri-sulfated galabioses. 2001. Carbohydrate research 335 (2001) pp. 167-180.*
Janczuk et al The synthesis of deoxy-a-Gal Epitope Derivatives for the Evaluation of an Anti—a-Gal Antibody Binding. 2002. Carbohydrate Research (2002) 337 pp. 1247-1259.*
Petitou et al. Experimental Proof for the Structure of a Thrombin-Inhibiting Heparin Molecule. 2001. Chem. Eur. J. 7(4) pp. 858-873.*
Medline MeSH database Trypanosomatina clasification introduced 1992.*
Database CAPLUS on STN, An 2001:544756, Espinola et al. "Synthetic Flux-Promoting Polyether Modstl: Cation Flux Dependence on Polyoxyethylene Chain Length", Isreal Journal of Chemistry. 2000, vol. 40, Issue 3-4.
Keller, C., Jol. Med. Chem., vol. 14, No. 10, pp. 936-940.

* cited by examiner

*Primary Examiner*—Shaojia Anna Jiang
*Assistant Examiner*—Traviss C. McIntosh, III
(74) *Attorney, Agent, or Firm*—Kent A. Herink; Daniel A. Rosenberg; Emily E. Harris

(57) ABSTRACT

The use of bicyclic carbohydrates for the treatment of parasite infections is described. Different bicyclic carbohydrates have been tested in vitro against a number of protozoa. These compounds also have been screened against viruses, tumors, bacteria and fungi. Compound A1, a thiophenyl-containing bicyclic carbohydrate possessed significant activity against *Trypanosoma brucei rhodiense*, a parasite that causes the lethal sleeping sickness. Compound A2 and Compound A3, bicyclic carbohydrates with halogen containing aryl groups, possessed significant activity against *Leishmania donovani*, a parasite that causes leishmaniasis. Bicyclic carbohydrates in general, and Compound A1, Compound A2 and Compound A3 more specifically, could be possible treatments for the sleeping sickness and leishmaniasis in the future.

6 Claims, 3 Drawing Sheets

BICYCLIC CARBOHYDRATES AS ANTIPROTOZOAL BIOACTIVE FOR THE TREATMENT OF INFECTIONS CAUSED BY PARASITES

This application claims priority to U.S. Ser. No. 60/438,474, filed on Jan. 7, 2003.

BACKGROUND OF THE INVENTION

The invention relates generally to bicyclic carbohydrates that are useful in the treatment of infections caused by parasites and, more specifically, to such compounds useful in the treatment or amelioration of infections caused by protozoa.

Protozoa are single-celled animals. Many species are important parasites of humans, the infections being most prevalent in tropical and subtropical regions, but also occurring in temperate regions. Transmission of protozoan parasites can occur in many ways, the two most common being injection by the bites of blood-sucking insects and accidental ingestion of infective stages. The geographic restriction of some species reflects both the distribution of vector insect species and the climatic conditions necessary for the parasites to complete their development in the insect. Orally acquired infections are favored by low standards of social and personal hygiene, and by increased survival of infective stages in warm damp conditions.

Protozoa infect body tissue and organs as intracellular parasites in a wide variety of cells or as extracellular parasites in the blood, intestine or urinogenital system.

One example of protozoa that cause diseases in humans are trypanosomes. Trypanosomes have been around for more than 300 million years. They are microscopic unicellular protozoa that are ubiquitous parasites of insects, plants, birds, bats, fish, amphibians and mammals. Because they have been around for so long, they and their natural hosts have evolved together to ensure their mutual survival. Trypanosomes can be found worldwide. Fortunately, few species of trypanosomes are pathogenic. Trypanosomes, and other parasites, mainly cause disease when they spread to new hosts, like humans and their domestic animals, especially recent imports into endemic areas of species that diverged since continents separated.

Generally trypanosomes are associated with diseases in Africa and South America. The related *Leishmania* organisms have a wider distribution. African trypanosomiasis is infection prevalent throughout Latin America, extending to the southern borders of the United States.

Transmission of human-infective trypanosomes occurs primarily through insects that feed upon us. The insect vectors, however, are very specific. The reason is that transmission usually requires the parasite to multiply and undergo specific developmental transitions in the insect. In fact, trypanosomes may originally have been purely parasites of insects. Adaptation to mammalian hosts was probably a late event in their evolution.

The African sleeping sickness, caused by trypanosomes, is transmitted to humans through the bite of the tsetse fly of the genus *Glossina*. There are two forms, each caused by a different parasite: *Trypanosoma brucei gambiense*, which causes a chronic infection lasting years and affecting countries of western and central Africa; and *Trypanosoma brucei rhodeseinse*, which causes acute illness lasting several weeks in countries of eastern and southern Africa.

Once inoculated into the human host by an infected tsetse fly, *T. brucei* proliferates and invades all organs. The host mounts an adaptive immune response which kills most of the invading parasites. But the trypanosome has the capacity to vary the composition of its surface coat protein antigens and thus a small number evade the immune system and multiply exponentially. The trypanosome can express thousands of variant proteins. The immune system eventually becomes exhausted by these repeated challenges, and the parasite develops in lymph and blood, causing a variety of debilitating conditions. The parasite can also invade the nervous system, leading to the characteristic "sleeping sickness" in which patients fall into a coma and die. The neurological alterations caused by trypanosomes are often irreversible even after successful treatment. Without treatment, the disease is invariably fatal.

The sleeping sickness is a daily threat to more than 60 million men, women and children in 36 countries of sub-Saharan Africa, 22 of which are among the least developed countries in the world. The estimated number of people thought to have the disease is between 300,000 and 500,000.

Most infected people only seek treatment when the disease has already advanced to the second stage. The most common treatment at this stage is melarsoprol (Arsobal, Specia), an archaic drug introduced in 1949. Melarsoprol contains arsenic, is extremely painful when injected, and kills outright 3–10% of patients treated. Furthermore, it is becoming less and less effective because the parasite has developed resistance to the drug. In some areas of Africa, such as Omugo, Uganda or Ibba, South Sudan where sleeping sickness programs are being ran, the drug fails to cure 25–30% of patients.

There is a safer, more effective alternative to melarsoprol called eflornithine (or DFMO). Its spectacular success at pulling people out of a coma led to its nickname, the "resurrection drug". However, Aventis ceased production in 1995, only five years after it first reached the market. Exclusively used to treat a disease of the poor, eflornithine was not profitable. Momentarily, WHO and Aventis have set up a program to combat the disease based on a three-point strategy: specific drug donation, disease management and research & development.

Although eflornithine is the only registered drug that can cure the melarsoprol-refractory form of the disease, nifurtimox (Lampit, Bayer) has also been used with good results.

Suramin (Germanin, Bayer) is considered the drug of choice for the therapy of early *Trypanosoma rhodesiense* sleeping sickness. However, it is a toxic drug that requires close medical supervision (WHO Expert Committee on Onchocerciasis. Technical Report Series #335. Geneva Switzerland: World Health Organization, 1966); its more severe side effects include immediate collapse and renal damage (Fain A. Toxic reactions after a single injection of bayer 205 given for prevention of trypanosomiasis. Rev Sc Med Cong Belge 1942:137; Chestenman C. The therapeutic effect of bayer 205 in trypanosomiasis of the central nervous system. Trans Soc Trop Med Hyg 1924;18:311). Also Bayer has agreed to provide a product (Germanin) to the WHO free of charge for an initial 5-year period. Suramin is no longer used as a prophylactic agent in African trypanosomiasis or as a therapeutic agent in early Gambian sleeping sickness because pentamidine (Lomodine, Pentam) is more effective in these situations (WHO Expert Committee on Trypanosomiasis, First Report, Technical Report Series #247. Geneva, Switzerland: World Health Organization, 1962).

According to the Website of Médecins Sans Frontières, it is unlikely that a new drug for sleeping sickness will be available in the near future (http://www.accessmed-msf.org/campaign/slp01.shtm). Except for eflornithine, whose effectiveness against sleeping sickness was discovered by chance, there has been no significant improvement in treatment for 50 years. In spite of the millions of people at risk, research into the human form of sleeping sickness is negligible. As is the case for other diseases such as river blindness and leishmaniasis, the veterinary industry may be the only hope, since the private sector is researching a form of the disease that infects cattle. This work may prove useful, as some of the drugs developed for the animal form of the disease may be effective in humans. But no drugs have been approved for human use and it will take a long time to study their effectiveness and obtain authorization for use. Some public funding has been allocated for research into a shorter treatment course for melarsoprol, but this toxic drug is still far from adequate.

Visceral leishmaniasis is caused by the protozoa *L. donovani*, named for William Leishman who first described it in London in 1903. The illness is distributed all over the world but predominantly is encountered in India, South America, Central Asia, Middle East and Africa. The spectrum of illness ranges from asymptomatic infection to severe life-threatening infection also known as kala azar, Dumdum fever, Black fever, Assam fever and infantile splenomegaly in various parts of the world.

The *Leishmania* species infecting humans are mainly *Leishmania donovani* causing visceral leishmaniasis and *Leishmania tropica* and *Leishmania brasiliensis* causing cutaneous leishmaniasis. *Leishmania* are obligatory intracellular parasites and are transmitted by the bite of a tiny 2- to 3-millimeter insect vector, the sandfly belonging to the genera *Phlebotomus* and *Lutzomyia*. The number of cases of leishmaniasis is increasing, mainly because of man-made environmental changes that increase human exposure to the sandfly vector. Another risk factor is the movement of susceptible populations into endemic areas, including large-scale migration of populations for economic reasons.

The parasite exists in 2 forms, the amastigote form and the promastigote form. The amastigote form occurs in humans, whereas the promastigote form occurs in the sandfly and in artificial culture. Only the female sandfly transmits the protozoa, infecting itself with the *Leishmania* parasites contained in the blood it sucks from its human or mammalian host. Resulting symptoms range from self-healing localized ulcers to widely disseminated progressive lesions of the skin, mucus membranes and the entire reticuloendothelial system. Parasitized macrophages disseminate infection to all parts of the body but more so to the spleen, liver and bone marrow. The spleen is enlarged with a thickening of the capsule, it is soft and fragile, its vascular spaces are dilated and engorged with blood, and the reticular cells of Billroth are increased markedly and packed with the amastigote forms of the parasite. However, no evidence of fibrosis is present. In the liver, the Kupffer cells are increased in size and number and infected with amastigote forms of *Leishmania*. Bone marrow turns hyperplastic, and parasitized macrophages replace the normal hemopoietic tissue. Leishmania sis infections are considered to be zoonotic diseases because the infection is being maintained in endemic areas in dogs, wild rodents and other animals.

Coexistence of leishmaniasis with HIV adds a serious dimension to the problem. Leishmaniasis is spreading in several areas of the world as a result of the rapidly spreading epidemic of AIDS. Co-infection with HIV has lead to the spread of leishmaniasis, typically a rural disease, into urban areas. In patients infected with HIV, leishmaniasis accelerates the onset of AIDS by cumulative immunosuppression and by stimulating the replication of the virus. It also may change asymptomatic *Leishmania* infections into symptomatic ones.

To overcome emerging resistance of protozoa against currently used medicines, new products are urgently needed.

SUMMARY OF THE INVENTION

The invention consists of the novel bicyclic carbohydrates, the generic structure of which is:

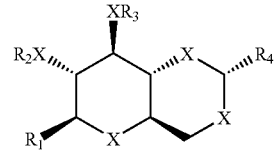

wherein $R_1$ is -Alkyl,-Aryl,-Benzyl, —XAlkyl or —XAryl; $R_2$ and $R_3$ are either -Alkyl,-Aryl, -Allyl, or —H; $R_4$ and $R_5$ form a ring and are either —CH(Ph)- or —CH(aryl)- and X is either O, N, or S, herein referred to as Formula A. Compounds of Formula A have activity against protozoa. The invention also includes analogs, pro-drugs and pharmaceutically acceptable salts thereof, together with pharmaceutical compositions for the prophylaxis and treatment of diseases caused by protozoa.

DETAILED DESCRIPTION OF A PREFERRED EMBODIMENT

Figure 1:
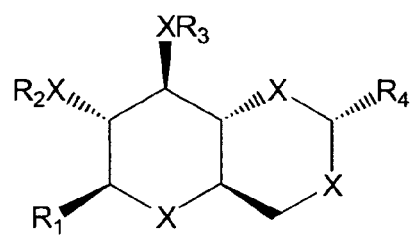
FIG. 1 is a chemical structure of the bicyclic carbohydrates of the present invention and designated Formula A.

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, acetate ascorbate, benzoate, citrate, etoglutarate, glycerophosphate, malonate, methanesulfonate, succinate, and tartarate. Suitable inorganic salts may also be formed, including bicarbonate, carbonate, hydrochloride, nitrate, and sulfate, salts.

Compounds of the present invention can conveniently be administered in a pharmaceutical composition containing the compound in combination with a suitable excipient, the composition being useful in combating protozoal infections. Depending on whether the preparation is used to treat internal or external protozoal infections, the compounds and compositions of the present invention can be administered parenterally, topically, orally, or rectally.

For parenteral administration, solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compound can be determined by comparing their in vitro activity. Methods for the extrapolation of effective dosages to humans are known to the art.

The compound is conveniently administered in unit dosage form; for example, containing 0.1 to 2000 mg, conveniently 100 to 1000 mg, most conveniently, 250 to 750 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

For internal infections, the compositions can be administered orally or parenterally at dose levels, calculated as the free base, of about 0.1 to 30 mg/kg, preferably 1 to 10 mg/kg of mammal body weight, and can be used in man in a unit dosage form, administered one to four times daily.

For parenteral administration, the compounds are presented in aqueous solution in a concentration of from about 0.1 to about 20%, more preferably about 1 to about 5%. The solution may contain other ingredients, such as emulsifiers, antioxidants or buffers.

The exact regimen for administration of the compound and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

Compounds of Formula A and pharmaceutically acceptable salts thereof are useful as antiprotozoal agents. Thus, they are useful to combat protozoal infections in animals, including man. The compounds are generally active against protozoa, and are particularly useful against the Trypanosomatidae and the Leishmania.

Materials and Methods

The bicyclic carbohydrates are synthesized as described below.

Synthesis of Compound A1

Figure 2:
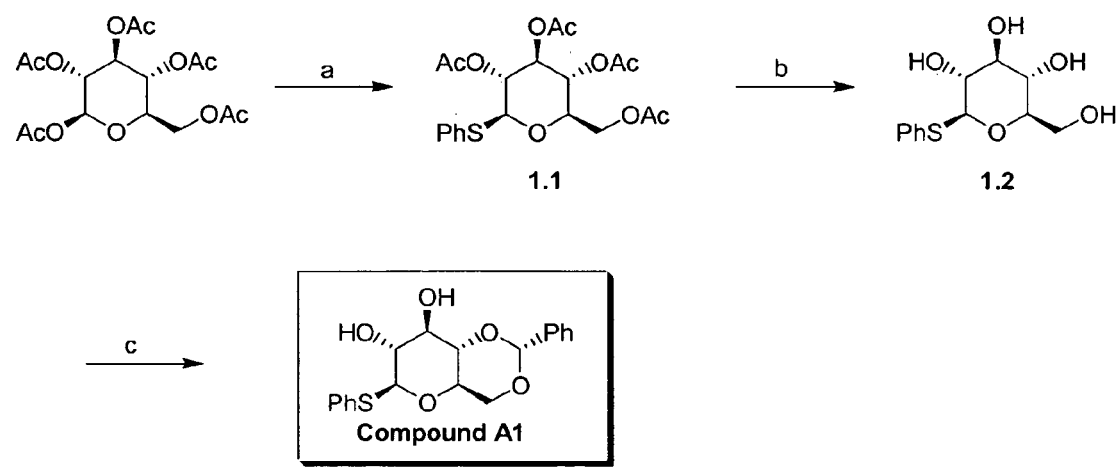
FIG. 2 is a diagrammatic representation of the scheme of synthesis of Compound A1.

The scheme of the synthesis of Compound A1 is illustrated in FIG. 2.

Synthesis of Compound 1.1

To a solution of β-D-glucose pentaacetate (150.0 g, 0.384 mol) in dry methylene chloride (1.65 l) were added thiophenol (43.5 ml, 0.423 mol) and tin(IV) chloride (50.0 ml, 0.268 mmol) at 0° C. The mixture was stirred at 0° C. for 15 minutes and at room temperature for 24 hours. Then it was diluted with methylene chloride (0.5 l), washed with a 1N hydrogen chloride solution (2×2 l), a saturated sodium bicarbonate solution (2×2 l) and brine (2×2 l). The organic layer was dried (MgSO$_4$), filtered and the solvent was removed under reduced pressure. The crude product was purified by recrystallization from dichloromethane/pentane to yield β-D-1-Deoxy-1-phenylthio-glucopyranosyl tetraacetate (131.2 g, 78%) as a white solid (Compound 1.1 of FIG. 2).

Formula: $C_{20}H_{24}O_9S$ Molecular weight: 440.46 $R_f$:0.31 (hexane/ethyl acetate 6/4) Melting point: 113–114° C. $[\alpha]_D^{20}$=−100.9; $[\alpha]_{365}^{20}$=−153.7 (c=1.12 in chloroform) IR(KBr): 1749, 1477, 1437, 1369, 1226, 1087, 1036, 908, 826, 744, 687 cm$^{-1}$ ES-MS: 463=[440+Na]$^{+1}$H-NMR (500 MHz, CDCl$_3$): δ 7.49 (2H, m), 7.31 (3H, m), 5.22 (1H, dd, app.t, J=9.4 Hz), 5.04 (1H, dd, app.t, J=9.8 Hz), 4.97 (1H, dd, app.t, J=9.7 Hz), 4.70 (1H, dd, J=10.1 Hz), 4.22 (1H, dd, J=12.3, 5.1 Hz), 4.18 (1H, dd, J=12.3, 2.5 Hz), 3.73 (1H, ddd, J=10.1, 5.1, 2.5 Hz), 2.09 (3H, s), 2.08 (3H, s), 2.01 (3H, s), 1.99 (3H, s) $^{13}$C-NMR (125 MHz, CDCl$_3$): δ 170.41, 170.03, 169.25, 169.10, 133.04, 131.56, 128.82, 128.30, 85.65, 75.73, 73.89, 69.89, 68.17, 62.06, 20.59, 20.43

Synthesis of Compound 1.2

β-D-1-Deoxy-1-phenylthio-glucopyranosyl tetraacetate (Compound 1.1) (440.5 g, 0.346 mol) was dissolved in a mixture of tetrahydrofuran and methanol (1:1, 1800 ml). To this solution potassium carbonate (11.0 g, 0.079 mol) was added at room temperature. The mixture was stirred at room temperature for 5 hours and filtered over silicagel. The residue was washed with methylene chloride/methanol (1:1, 1000 ml) and the solvent was removed to yield β-D-1-Deoxy-1-phenylthioglucopyranose (94.0 g, 99%) as a white solid, Compound 1.2.

Formula: $C_{12}H_{16}O_5S$ Molecular weight: 272.31 $R_f$:0.50 (dichloromethane/methanol 8/2) Melting point: 104–105° C. $[\alpha]_D^{20}$=−106.4; $[\alpha]_{365}^{20}$=−236.1 (c=1.30 in chloroform) IR(KBr): 3405, 1583, 1480, 1439, 1274, 1024, 879, 819, 742, 691 cm$^{-1}$ ES-MS: 295=[272+Na]$^{+1}$H-NMR (500 MHz, CD$_3$OD): δ 7.56 (2H, m), 7.26 (3H, m), 4.59 (1H, d, J=9.8 Hz), 3.86 (1H, dd, J=12.0, 1.8 Hz), 3.38 (1H, dd, app.t, J=8.6 Hz), 3.30 (2H, m), 3.26 (1H, dd, J=12.0, 5.4 Hz), 3.21 (1H, dd, J=9.7, 8.7 Hz) $^{13}$C-NMR (125 MHz, CDCl$_3$): δ 135.26, 132.75, 129.66, 128.32, 89.42, 82.05, 79.71, 73.79, 71.40, 62.70

Synthesis of Compound A1

To a solution of a β-D-1-deoxy-1-phenylthioglucopyranose (Compound 1.2) (81.2 g, 0.298 mol) in dry dimethylformamide (325 ml) were added camphorsulfonic acid (17.3 g, 0.074 mol) and benzaldehyde dimethyl acetal (50.0 ml, 0.358 mol) at room temperature. The mixture was heated at 110° C. and stirred for 48 hours. The reaction mixture was cooled to room temperature, diluted with ethyl acetate (1000 ml), washed with a 1N sodium hydroxide solution (2×500 ml), a saturated sodium bicarbonate solution (2×500 ml) and brine (2×500 ml). The organic layer was dried (MgSO$_4$), filtered and the solvent was removed under reduced pressure. The crude product was purified by recrystallization from ethyl acetate/hexane to yield benzylidene acetal (79.4 g, 74%) as a white solid, illustrated in FIG. 2 as Compound A1.

Formula: $C_{19}H_{20}O_5S$ Molecular weight: 360.42 $R_f$: 0.16 (dichloromethane/methanol 98:2) Melting point: 172–174° C. $[\alpha]_D^{20}$=+27.8; $[\alpha]_{365}^{20}$=−60.4 (c=1.07 in chloroform) IR(KBr): 3372, 2880, 1652, 1440, 1370, 1296, 1277, 1215, 1166, 1106, 1070, 1010, 986, 831, 743, 698, 654 cm$^{-1}$ ES-MS: 383=[360+Na]$^{+1}$H-NMR (500 MHz, CDCl$_3$): δ 7.52 (2H, m), 7.50 (2H, m), 7.32 (6H, m), 5.56 (1H, s), 4.70 (1H, d, J=9.8 Hz), 4.27 (1H, dd, J=10.3, 4.8 Hz), 3.76 (1H, dd, app. t, J=10.0 Hz), 3.65 (1H, dd, app.t, J=8.9, 8.7 Hz), 3.50 (1H, dd, app.t, J=9.7, 4.9 Hz), 3.43 (2H, m) $^{13}$C-NMR (125 MHz, CDCl$_3$): δ 136.78, 132.95, 131.26, 129.21, 129.01, 128.34, 128.24, 126.17, 101.72, 88.49, 80.11, 74.50, 72.53, 70.45, 66.47

Synthesis of Compound A2

Figure 3:
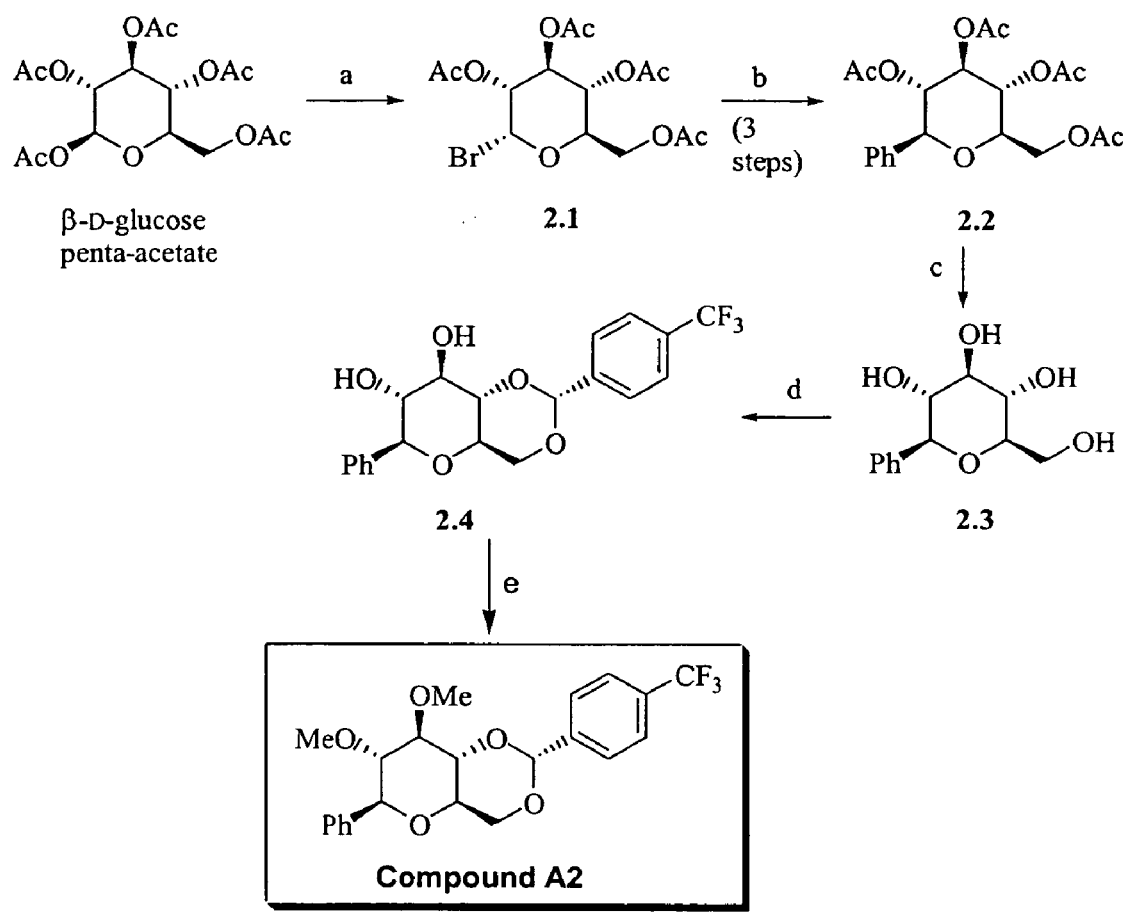
FIG. 3 is a diagrammatic representation of the scheme of synthesis of Compound A2.

The scheme of the synthesis of Compound A2 is illustrated in FIG. 3.

Synthesis of Compound 2.1

To (β)-D-glucose penta-acetate (24.6 g, 63.0 mmol) was added a solution of hydrogen bromide in acetic acid (33 wt %, 100 ml). A dark brown color immediately appears. The reaction mixture was stirred at room temperature for 30 minutes under argon atmosphere. Subsequently the solvent was removed by azeotropic distillation in vacuo with toluene (4×50 ml), yielding a green-brown solid Compound 2.1. The crude product was used in the next reaction step without further purification.

Formula: $C_{14}H_{19}O_9Br$ Molecular weight: 411.20 $R_f$:0.46 (cyclohexane/ethyl acetate 1:1) IR(KBr): 2962, 2360, 2342, 1748, 1435, 1369, 1218, 1162, 1112, 1079, 1042, 911, 752, 668, 601, 563 $cm^{-1}$ ES-MS: 433=[410+Na]$^+$, 435=[412+Na$^+$]$^1$H-NMR (500 MHz, CDCl$_3$): [δ (ppm); J (Hz)] 6.61 (1H, d, J=4.0), 5.56 (1H, dd app. t, J=9.7), 5.16 (1H, dd, app. t, J=9.7), 4.84 (1H, dd, J=10.0, 4.0), 4.33 (1H, m), 4.30 (1H, m), 4.13 (1H, dd, J=12.3, 1.5), 2.11 (3H, s), 2.10 (3H, s), 2.05 (3H, s), 2.03 (3H, s) $^{13}$C-NMR (125 MHz, CDCl$_3$): [δ (ppm)] 170.37, 169.70, 169.64, 169.31, 86.34, 71.91, 70.39, 69.94, 66.94, 60.76, 20.48, 20.48, 20.38, 20.38

Synthesis of Compound 2.2

To a solution of phenyl magnesium bromide (200 ml of a 3M solution in diethyl ether, 600 mmol, 9.5 eq) in dry diethyl ether (500 ml), cooled to 0° C., was added a solution of the bromide, Compound 2.1 (63.0 mmol theoretical) in dry diethyl ether (500 ml) by canulation. The reaction mixture was stirred at room temperature under argon-atmosphere for 72 hours. Subsequently the reaction mixture was poured out into water (2000 ml), and acetic acid (200 ml) was added to dissolve the magnesium salts. The two layers were separated and the organic layer was washed with water (3×500 ml). The combined aqueous layers were concentrated under reduced pressure to yield a light brown solid residue. This residue was dissolved in pyridine (500 ml). At 0° C., acetic anhydride (340 ml) was added slowly. After adding DMAP (200 mg, 1.64 mmol), stirring was continued for 20 hours at room temperature under argon-atmosphere. Next the reaction mixture was concentrated under reduced pressure, followed by azeotropic distillation with toluene (1×250 ml), and the addition of diethyl ether (3 l). The obtained organic layer was washed with sat. NaHCO$_3$-sol. (2×1 l), 1 N HCl-sol. (2×1 l) and water (2×1 l). Drying on MgSO$_4$, and concentrating under reduced pressure, yielded 25.1 g light brown crystals. These were purified by recrystallization from 2-propanol, to give 16.1 g of Compound 2.2 (63%) as white crystals.

Formula: $C_{20}H_{24}O_9$ Molecular weight: 408.40 $R_f$:0.42 (cyclohexane/ethyl acetate 1:1) Melting point: 149–150° C. IR (KBr): 2956, 1753, 1433, 1368, 1224, 1104, 1036, 978, 916, 764, 738, 702, 603 $cm^{-1}$ ES-MS: 431=[408+Na]$^{+1}$H-NMR (500 MHz, CDCl$_3$): [δ (ppm); J (Hz)] 7.39 (5H, m), 5.24 (1H, dd, app. t, J=9.4), 5.24 (1H, dd, app. t, J=9.8), 5.14 (1H, dd, app. t, J=9.8), 4.40 (1H, d, J=9.9),4.30 (1H, dd, J=17.2, 4.7), 4.16 (1H, dd, J=12.2, 1.5), 3.85 (1H, m), 2.09 (3H, s), 2.06 (3H, s), 2.01 (3H, s), 1.80 (3H, s) $^{13}$C-NMR (125 MHz, CDCl$_3$): [δ (ppm)] 170.60, 170.25, 169.36, 168.70, 136.01, 128.75, 128.28, 126.96, 80.08, 75.94, 74.06, 72.44, 68.39, 62.17, 20.61, 20.48, 20.21

Synthesis of Compound 2.3

To a solution of the tetra-acetate, Compound 2.2, (16.08 g, 39.4 mmol) in a mixture of tetrahydrofuran (232 ml) and methanol (232 ml) was added anhydric potassium carbonate (1.36 g, 9.84 mmol, 0.25 eq). The mixture was stirred at room temperature under argon-atmosphere for 3 hours. Silicagel (40 ml) was added and the solvent was removed under reduced pressure. Purification of the product by column chromatography (dichloromethane/methanol 85/15) gives 9.50 g of product Compound 2.3 (99%).

Formula: $C_{12}H_{16}O_5$ Molecular weight: 240.26 $R_f$: 0.12 (dichloromethane/methanol 9:1) IR (KBr): 3368, 2919, 2360, 1636, 1496, 1455, 1082, 1042, 891, 764, 701, 595 $cm^{-1}$ ES-MS: 258=[240+NH$_4$]$^+$, 263=[240+Na]$^{+1}$H-NMR (500 MHz, CDCl$_3$): [δ (ppm); J (Hz)] 7.44 (2H, d, J=7.1), 7.35 (2H, dd, app. t, J=7.6), 7.30 (1H, m), 4.15 (1H, d, J=9.4), 3.90 (1H, dd, J=12.1, 1.6), 3.72 (1H, dd, J=12.0, 5.2), 3.51 (1H, dd, app. t, J=8.7), 3.45 (1H, dd, app. t, J=9.4), 3.43 (3H, m), 3.40 (1H, dd, app. t, J=9.2) $^{13}$C-NMR (125 MHz, CDCl$_3$): [δ (ppm)] 139.30, 127.43, 82.41, 80.70, 78.23, 74.98, 70.40, 61.41

Synthesis of Compound 2.4

To CSA (30 mg; 0.125 mmol; 0.1 eq.) and anhydrous CuSO$_4$ (300 mg; 1.880 mmol; 1.5 eq.) a solution of tetrol (300 mg; 1.248 mmol) in dry acetonitrile (12 ml) is added. Then α,α,α-trifluortolualdehyde (900 μl; 6.240 mmol; 5 eq.) is added drop-wise and the reaction mixture is kept at 90° C. After reflux for 23 hours the reaction mixture is poured in water (50 ml). The water phase is extracted 3 times with CH$_2$Cl$_2$ (3×50 ml). The combined organic phases are washed with brine (50 ml), neutralized with Et$_3$N and dried over MgSO$_4$. The residue is purified by column chromatography (Merck kieselgel; CH$_2$Cl$_2$/iPrOH: 98/2). Compound 2.4 is obtained in 77% yield (382 mg; 0.964 mmol).

Formula: $C_{20}H_{19}O_5F_3$ Molecular weight: 396.4 $R_f$:0.21 (CH$_2$Cl$_2$/iPrOH: 98/2) Melting point: 175° C. $[α]_D^{20}$: −19.96° (c=1.080; CHCl$_3$) IR (KBr-disc, film): (cm$^{-1}$) 3394 (m); 3066 (w); 3033 (w); 2990 (w); 2880 (w); 1324 (s); 1167(m); 1111 (s); 1068 (s); 1035 (m); 1018 (m); 832 (m); 702 (m) MS (m/z): 60 (36); 77 (37); 91 (68); 107 (100); 127 (28); 173 (34); 175 (27); 179 (13); 217 (6); 377 (3); 396 (4; M$^{+°}$)$^1$H-NMR (500 MHz; CD$_3$COCD$_3$): [δ (ppm); J (Hz)] 7.76 (2H; d; J=8.8); 7.73 (2H; d; J=8.8); 7.41 (2H; m); 7.25–7.35 (3H; m); 5.75 (1H; s); 4.59 (1H; d; J=3.3); 4.33 (1H; d; J=9.5); 4.27 (1H; dd; J=4.9, 10.2); 4.21 (1H; d; J=4.8); 3.81 (1H; t; J=10.2); 3.78 (1H; m); 3.67 (1H; dd(app.t); J=9.2); 3.61 (1H; ddd; J=4.9, 9.6, 9.6); 3.54 (1H; ddd; J=4.9, 9.0, 9.0) APT (125 MHz; CD$_3$COCD$_3$): [δ (ppm)] 68.9 (CH$_2$); 71.0 (CH); 75.4 (CH); 76.3 (CH); 81.9 (CH); 83.1 (CH); 100.4 (CH); 121.4, 123.6, 125.7, 127.9 (q; C); 125.2 (CH); 127.5 (CH); 128.0 (CH); 128.0 (CH); 128.1 (CH); 130.1, 130.4, 130.6, 130.9 (q; C); 140.0 (C); 142.7 (C)

Synthesis of Compound A2

To an ice-cooled solution of Compound 2.4 (150 mg; 0.378 mmol) in dry DMF (3.78 ml) NaH (60% dispersion in mineral oil; 61 mg; 1.514 mmol; 4 eq.) is added. After stirring for 30 minutes under argon atmosphere at 0° C., methyl iodide (118 μl; 1.892 mmol; 5 eq.) is added drop-wise and the ice bath is removed. The reaction mixture is stirred further for 16 hours at room temperature under argon atmosphere. The reaction mixture is then poured in H$_2$O (50 ml) and the water phase is extracted 3 times with ether (3×50 ml). The combined organic phases are washed once with brine (50 ml) and dried over MgSO$_4$. The residue is purified by column chromatography (Merck kieselgel; CHCl$_3$). Compound A2 is obtained with a yield of 92% (147 mg; 0.346 mmol).

Formula: $C_{22}H_{23}O_5F_3$ Molecular weight: 424.4 $R_f$: 0.40 (CHCl$_3$/ether: 99.5/0.5) Melting point: 125–126° C. $[α]_D^{20}$: −20.06° (c=1.040; CHCl$_3$) IR (KBr-disc, film): (cm$^{-1}$) 3063 (w); 3030 (w); 2987 (w); 2932 (w); 2892 (w); 2834 (w); 1324 (s); 1169 (s); 1109 (s); 1093 (s); 1068 (s); 1018 (m); 828 (m); 701 (m) MS (m/z): 88 (43); 91 (15); 121 (100); 173

(11); 217 (10); 303 (2); 405 (<1) $^1$H-NMR (500 MHz; CD$_3$COCD$_3$): [δ (ppm); J (Hz)] 7.73 (4H; s(2 gedeg. d); 7.41 (2H; M); (7.34 (3H; m); 5.76 (1H; s); 4.29 (1H; d; J=9.7); 4.27 (1H; dd; J=5.0, 10.2); 3.80 (1H; dd(app.t); J=10.2); 3.75 (1H; dd(app.t); J=9.3); 3.58 (3H; s); 3.58 (1H; m); 3.50 (1H; dd(app.t); J=8.9); 3.16 (1H; dd; J=8.6, 9.4); 3.01 (3H; s) APT (125 MHz; CD$_3$COCD$_3$): [δ (ppm)] 60.1 (CH$_3$); 60.1 (CH$_3$); 68.9 (CH$_2$); 70.7 (CH); 82.2 (CH); 82.3 (CH); 84.8 (CH); 85.7 (CH); 100.2 (CH); 121.4, 123.6, 125.7, 127.9 (q; C); 125.3 (CH); 127.3 (CH); 127.9 (CH); 128.3 (CH); 130.2, 130.4, 130.7, 130.9 (q; C); 139.8 (C); 142.6 (C)

Synthesis of Compound A3

Figure 4:
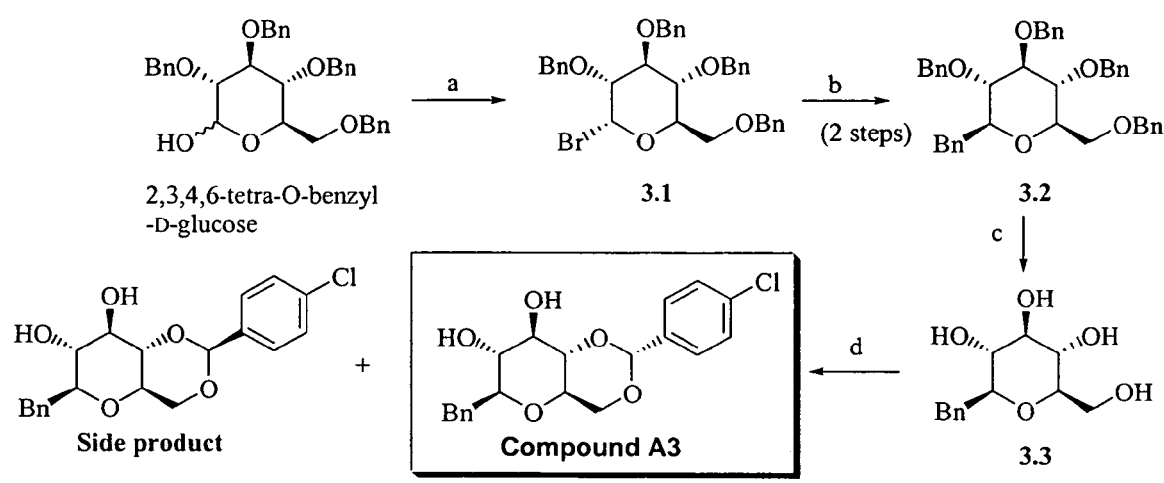
FIG. 4 is a diagrammatic representation of the scheme of synthesis of Compound A3.

The scheme of the synthesis of Compound A3 is illustrated in FIG. 4.

Synthesis of Compound 3.1

To a solution of 2,3,4,6-tetra-O-benzyl-D-glucose (10.0 g, 18.5 mmol) in CH$_2$Cl$_2$ (125 ml) and DMF (6.25 ml) is added drop-wise at room temperature a solution of oxalyl bromide (2.5 ml of a 10 M sol. in CH$_2$Cl$_2$, 1.35 eq). This is followed by a vigorous formation of gas. The reaction mixture is stirred at room temperature for 60 minutes under Ar atmosphere. Then the reaction mixture is poured in iced water (125 ml). After separation of the layers, the organic phase is washed with iced water (2×125 ml). Drying over MgSO$_4$, filtration and concentration in vacuo yields a yellow oil, Compound 3.1, that is used in the next reaction without further purification.

Formula: C$_{34}$H$_{35}$BrO$_5$ Molecular weight: 603.55 R$_f$: 0.53 (cyclohexaan/ethylacetaat 85:15) $^1$H-NMR (500 MHz, CDCl$_3$): [δ (ppm); J (Hz)] 7.37 (3H$_1$, m), 7.33 (5H, m), 7.31 (5H, M), 7.28 (5H, m), 7.15 (2H, m), 6.43 (1H, d, J=3.7), 4.98 (1H, d, J=5.0), 4.83 (2H, dd, app. t, J=10.9), 4.58 (1H, d, J=12.1), 4.50 (1H, d, J=10.7), 4.46 (2H, d, J=12.1), 4.06 (1H, m), 4.03 (1H, dd, app. t, J=9.2), 3.80 (1H, m), 3.78 (1H, m), 3.76 (1H, d, J=4.6), 3.65 (1H, dd, J=11.0, 2.0), 3.54(1H, dd, J=9.2, 3.7)

Synthesis of Compound 3.2

To a solution of Compound 3.1 (18.5 mmol theoretically) in dry Et$_2$O (250 ml), cooled to 0° C., is added slowly benzylmagnesium chloride (150 ml of a 1M-sol. in Et$_2$O, 8 eq). The mixture is stirred at 0° C. for 1 hour, after which the temperature was elevated slowly to room temperature. After overnight stirring at room temperature, the reaction mixture is poured in H$_2$O (500 ml) and AcOH, after which the phases are separated. The organic phase is then washed with 3×500 ml sat. NaHCO$_3$-sol. and 250 ml sat. NaCl-sol. Drying over MgSO$_4$, filtration and concentrating in vacuo yields the crude product. This product is then purified by column chromatography (60–230 mesh silica, gradient: toluene:cyclohexane 8:2, toluene, cyclohexane:ethyl acetate 9:1), yields 6.47 g of Compound 3.2 (57% over 2 steps) as a colorless oil.

Formula: C$_{41}$H$_{42}$O$_5$ Molecular weight: 614.78 R$_f$:0.15 (cyclohexane/diethyl ether 9:1) [α]$_D^{20}$=+85.3°; [α]$_{365}^{20}$=+88.1°(c=0.60 in chloroform) IR(KBr): (cm$^{-1}$)2862, 2360, 1604, 1496, 1454, 1360, 1209, 1085, 1028, 735, 697, 668 ES-MS: 632=[M+NH$_4$]$^{+1}$H-NMR (500 MHz, CDCl$_3$): [δ (ppm); J (Hz)] 7.36 (5H, m), 7.34 (5H, m), 7.31 (5H, M), 7.29 (5H, m), 7.26 (2H, m), 7.22 (3H, m), 4.96 (1H, d, J=11.0), 4.95 (1H, d, J=11.0), 4.91 (1H, d, J=11.0), 4.84 (1H, d, J=10.8), 4.69 (1H, d, J=11.0), 4.62 (1H, d, J=10.8), 4.59 (1H, d, J=12.2), 4.52 (1H, d, J=12.2), 3.74 (1H, dd, app. t, J=9.0), 3.69 (1H, m), 3.68 (1H, m), 3.66 (1H, dd, app. t, J=9.3), 3.52 (1H, ddd, J=18.3, 9.2, 2.3), 3.37 (1H, dd, app. t, J=9.0), 3.36 (1H, m), 3.17 (1H, dd, J=14.3, 2.0), 2.75 (1H, dd, J=14.3, 8.8) APT-NMR (125 MHz, CDCl$_3$): [δ (ppm)] 138.9 (C), 138.7 (C), 138.5 (C), 138.3 (C), 138.2 (C), 129.7 (CH), 128.6 (CH), 128.6 (CH), 128.5 (CH), 128.4 (CH), 128.2 (CH), 128.0 (CH), 127.9 (CH), 127.8 (CH), 127.7 (CH), 127.6 (CH), 126.2 (CH), 87.5 (CH), 81.8 (CH), 80.1 (CH), 79.0 (CH), 78.7 (CH), 75.7 (CH$_2$), 75.2 (CH$_2$), 75.1 (CH$_2$), 73.5 (CH$_2$), 69.0 (CH$_2$), 38.0 (CH$_2$)

Synthesis of Compound 3.3

To a solution of Compound 3.2 (6.0 g, 9.76 mmol) in absolute EtOH (240 ml) is added at room temperature Pd on carbon (600 mg, 10 mol %). The reaction mixture is shaken for 5 hours in a Parr apparatus under 4 atm H$_2$-gas. Filtration over celite and concentration in vacuo yields 2.62 g residue as white-yellow foam. Purification of this product by column chromatography (60–230 mesh, CH$_2$Cl$_2$:MeOH 9:1) yields 2.46 g of Compound 3.3 as white foam (99%)

Formula: C$_{13}$H$_{18}$O$_5$ Molecular weight: 254.28 R$_f$: 0.14 (dichloromethane/methanol 9:1) IR(KBr): (cm$^{-1}$) 3381, 2922, 2360, 2341, 1641, 1603, 1496, 1454, 1379, 1308, 1226, 1079, 1031, 897, 754, 701, 668 ES-MS: 272=[254+NH$_4$]$^{+1}$H-NMR (500 MHz, CDCl$_3$): [δ (ppm); J (Hz)] 7.29 (2H, d, J=7.0), 7.22 (2H, dd, app. t, J=7.3), 7.14 (1H, m), 3.75 (1H, dd, J=11.9, 2.4), 3.60 (1H, dd, J=11.8, 5.4), 3.35 (1H, m), 3.32 (1H, m), 3.25 (1H, dd, app. t, J=9.4), 3.15 (1H, m), 3.12 (1H, m), 3.09 (1H, dd, app. t, J=9.3), 2.69 (1H, dd, J=14.5, 8.5) APT-NMR (125 MHz, CD$_3$OD): [δ (ppm)] 139.1 (C), 129.4 (CH), 127.6 (CH), 125.6 (CH), 80.4 (CH), 80.1 (CH), 78.6 (CH), 73.7 (CH), 70.6 (CH), 61.6 (CH$_2$), 37.4 (CH$_2$)

Synthesis of Compound A3.

To a solution of β-D-1-deoxy-1-benzyl-glucose (Compound 3.3) (500 mg, 1.97 mmol) and p-chlorobenzaldehyde (1.38 g, 5 eq) in acetonitrile (12 ml), anhydrous copper(II) sulfate (942 mg, 3 eq) and CSA (46 mg, 0.1 eq) are successively added. The reaction mixture is heated to reflux temperature, and refluxed overnight under Ar-atmosphere while stirring. After TLC-analysis additional 2 eq p-chlorobenzaldehyde and 0.1 eq CSA are added. After reflux for 4 hours the reaction mixture is poured in H$_2$O (100 ml), followed by extraction with CH$_2$Cl$_2$ (3×100 ml). The combined organic phases are washed with brine (150 ml) and dried over MgSO$_4$. Filtration and concentration in vacuo yields a yellow-brown solid residue. Purification by column chromatography (60–230 mesh silica, CH$_2$Cl$_2$:iPrOH 97:3) and a purification via HPLC (CH$_2$Cl$_2$:iPrOH 97:3) yield 596 mg Compound A3 (80%) and 20 mg of the other isomer (3%).

Main Product

Formul: C$_{20}$H$_{21}$ClO$_5$ Molecular weight: 376.83 R$_f$:0.25 (CH$_2$Cl$_2$:iPrOH 97:3) Melting point: 106–108° C. [α]$_D^{20}$=−33.4°; [α]$_{365}^{20}$=−105.0°(c=1.02 in chloroform) IR (KBr): (cm$^{-1}$) 3390 (br), 2921 (m), 2867 (m), 1497 (m), 1377 (m), 1121 (s), 1088 (s), 1023 (m), 1016 (s), 1006 (s), 974 (m), 819 (m), 700 (m) EI-MS: (m/z) 57 (23), 91 (100), 105 (33), 141 (51), 163 (5), 179 (5), 213 (4), 236 (3), 285 (6), 376 (23) [M$^+$]ES-MS: 377 [M+H$^+$], 399 [M+Na$^+$]$^1$H-NMR (500 MHz, CDCl$_3$): [δ (ppm); J (Hz)] 7.42 (2H, d, J=8.5), 7.35–7.33 (2H, M), (7.31–7.22 (5H, m), 5.47 (1H, s), 4.27 (1H, dd, J=10.4, 4.9), 3.74 (1H; dd; app t, J=8.8), 3.66 (1H, dd, app t, J=10.2), 3.58 (1H, ddd, J=9.2, 8.0, 2.7), 3.42 (1H, dd, app t, J=9.2), 3.38 (1H, dd, app t, J=9.7), 3.36 (1H, ddd, app dt, J=9.7, 4.9), 3.18 (1H, dd, J=14.4, 2.6), 2.80 (1H, dd, J=14.4, 8.0), 2.79 (1H, s), 2.59 (1H, d, J=2.7) APT-NMR (125 MHz, CDCl$_3$): [δ (ppm)] 137.9 (C), 135.6 (C), 135.2 (C), 129.8 (CH), 128.6 (CH), 128.2 (CH), 127.8 (CH), 126.4

(CH), 101.0 (CH), 81.1 (CH), 80.3 (CH), 75.4 (CH), 73.8 (CH), 70.1 (CH), 68.9 (CH$_2$), 37.9 (CH$_2$)

Side Product

Formula: C$_{20}$H$_{21}$ClO$_5$ Molecular weight: 376.83 R$_f$:0.25 (CH$_2$Cl$_2$:iPrOH 97:3) Melting point: 184–186° C. [α]$_D^{20}$=+ 112.4°; [α]$_{365}^{20}$=+377.0°(c=0.46 in chloroform) IR (KBr): (cm$^{-1}$) 3369 (br), 2911 (m), 1497 (m), 1371 (m), 1339 (m), 1110 (s), 1083 (s), 1028 (m), 1017 (s), 1001 (s), 979 (m), 946 (m), 827 (m), 810 (m), 739 (m), 696 (m) EI-MS: (m/z) 57 (26), 91 (100), 105 (26), 141 (66), 175 (5), 179 (5), 213 (6), 243 (6), 285 (10), 376 (8) [M$^+$]ES-MS: 377 [M+H$^+$], 399 [M+Na$^+$]$^1$H-NMR (500 MHz, CDCl$_3$): [δ (ppm); J (Hz)] 7, 46 (2H, d, J=8.5), 7.37 (2H, d, J=8.5), 7.33–7.30 (2H, m), 7.26–7.23 (3H, m), 5.51 (1H, s), 4.35–4.33 (1H, m), 4.18 (1H, dd, J=10.5, 4.9), 3.99–3.96 (2H, m), 3.84 (1H, ddd, app dt, J=9.7, 4.9), 3.64 (1H, dd, app t, J=10.2), 3.53–3.47 (1H, m), 3.13 (1H, dd, J=14.9, 3.2), 2.98 (1H, dd, J=14.9, 11.6), 2.78 (1H, br s), 2.67(1H, br s) APT-NMR (125 MHz, CDCl$_3$): [δ (ppm)] 138.5 (C), 135.6 (C), 135.2 (C), 129.0 (CH), 128.6 (CH), 128.6 (CH), 127.8 (CH), 126.4 (CH), 101.2 (CH), 82.0 (CH), 78.0 (CH), 72.4 (CH), 71.7 (CH), 69.2 (CH$_2$), 63.7 (CH).

BIOLOGICAL ACTIVITY
Features of Medically Important Protozoa

| Location | Species | Mode of transmission | Disease |
|---|---|---|---|
| Intestinal tract | Entamoeba histolytica Giardia lamblia Cryptosporidium spp. | Ingestion of cysts in food | Amebiasis Giardiasis Cryptosporidiosis |
| Urinogenital tract | Trichomonas vaginalis | Sexual | Trichomoniasis |
| Blood and tissue | Trypanosome spp. | | |
| | T. cruzi | Reduviid bug | Trypanosomiasis Chagas' disease |
| | T. gambiense T. rhodesiense Leishmania spp. | Tsetse fly | Sleeping sickness |
| | L. donovani | Sand fly | Visceral leishmaniasis (kala-azar) |
| | L. tropica, L. mexicana, L. braziliensis | Sand fly | cutaneous leishmaniasis, mucocutaneous leishmaniasis |
| | Plasmodium spp. | | |
| | P. vivax, P. ovale, P. malariae, P. falciparium | Anopheles mosquito | Malaria |
| | Toxoplasma gondii | Ingestion of cysts in raw meat; contact with soil contaminated by cat faeces | Toxoplasmosis |
| | Pneumocystis carinii | Inhalation | pneumonia |

Here we describe the use of bicyclic carbohydrates for the treatment of parasite infections, by means of two examples: the treatment of sleeping disease caused by *Trypanosoma* spp. and in the second part the treatment of leishmaniasis caused by *Leishmania* spp.

EXAMPLE 1

The Activity of Compound A1 against *Trypanosoma brucei* Causing Sleeping Sickness Compound A1 was screened against *Trypanosoma brucei* by World Health Organization (Switzerland) using its established screening service. The results of the screening by WHO are presented in Table 1.

TABLE 1

Screening results of Compound A1 against protozoa

| | IC$_{50}$ (μM) | | | |
|---|---|---|---|---|
| Compound | P. falciparum | T. cruzi | T. brucei rhodesiense | Cytox (μM) |
| Compound A1 | 22,384 | >32 | 0.187 | >32 |
| Suramin | — | — | 0.21 | — |
| Nifurtimox | — | 1.24 | — | — |
| Chloroquine | 0.014 | — | — | — |

Results are given as micromolar concentrations that produced 50% inhibition ('IC$_{50}$') in the assays used.
A cytotoxicity assay on a human cell line (MRC-5) was performed (Cytox)

EXAMPLE 2

The Activity of Compound A2 and Compound A3 against *Leishmania donovani* Causing Leishmaniasis.

One strain of *Leishmania* spp. (*Leishmania.donovani* MHOM/ET/67/L82) is used. The strain is maintained in the hamster. Amastigotes are collected from the spleen of an infected hamster and spleen parasite burden is assessed using the Stauber technique or amastigotes are counted in the haemocytometer after 1:100 dilution in trypan blue.

Primary peritoneal mouse (CDI or NMRI) macrophages are collected 1 day after a macrophage production stimulation with an i.p injection of 2 ml of 2% starch in distilled water. All cultures and assays are conducted at 37° C. under an atmosphere of 5% CO$_2$. Ten mg/ml compound stock solutions are prepared as advised by the supplier, otherwise dissolved in 100% DMSO. Stock solutions are kept at 4° C. for a maximum of 2 weeks, thereafter at −20° C. The compounds are pre-diluted to 1 mg/ml. Assays are performed in sterile 16-well tissue culture slides, each well containing 100 μl of the compound dilutions together with 100 μl of macrophage/parasite inoculum (4×10$^5$ macrophages/ml and 1.2×10$^6$ parasites/ml). The inoculum is prepared in RPMI-1640 medium, supplemented with 10% heat inactivated fetal calf serum. Parasite growth is compared to control wells (100% parasite growth). After 96 hours of incubation, parasite growth is microscopically assessed after staining the cells with a 10% Giemsa solution. The results are expressed as IC$_{50}$ calculated by linear regression analysis. The compounds are tested in duplicate at 2 concentrations (30-10 μg/ml). Miltefosine is included as the reference drug. The compound is classified as inactive when the IC$_{50}$ is higher than 10 μg/ml. When IC$_{50}$ lies between 1 and 10 μg/ml, the compound is regarded as being moderate active. When the IC$_{50}$ is lower than 1 μg/ml, the compound is classified as highly active and is further evaluated in a secondary screening.

TABLE 2

Screening results of Compounds A2 and A3 against protozoa

| Compound | IC$_{50}$ (μM) | | | | |
|---|---|---|---|---|---|
| | P. falciparum | T. cruzi | T. brucei rhodesiense | L. donovani | L-6 |
| Compound A2 | 11.5 | 33.4 | 33.9 | 1.01 | 31.6 |
| Compound A3 | >13.3 | 14.3 | 20.4 | <0.98 | 60 |
| Chloroquine | 0.005 | — | — | — | — |
| Miltefosine | — | — | — | 0.47 | — |
| Melarsoprol | — | — | 0.01 | — | — |
| Benznidazole | — | 1.29 | — | — | — |

Results are given as micromolar concentrations that produced 50% inhibition ('IC$_{50}$') in the assays used.
A cytotoxicity assay on L-6 mammalian cells was performed (L-6)

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

What is claimed is:

1. A method of treating a protozoal infection in a mammalian subject comprising the step of administering to the subject a composition comprising at least one compound of the formula:

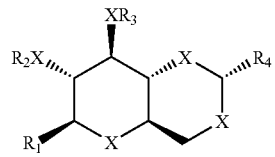

wherein:
R$_1$ is selected from the group consisting of alkyl, -aryl, -benzyl, -SAlkyl and -SAryl;
R$_2$ and R$_3$ are identical and are selected from the group consisting of -alkyl, -aryl, -allyl and —H;
R$_4$ is selected from the group consisting of phenyl and aryl; and
X is;
or a pharmaceutically active salt thereof.

2. A method as defined in claim 1, wherein R$_1$ preferably is selected from the group consisting of phenyl, benzyl and thiophenyl; R$_2$ and R$_3$ are identical and are selected from the group consisting of methyl and hydrogen; R$_4$ is selected from the group consisting of phenyl, 4-chlorophenyl and 4-trifluoromethylphenyl; and X is O; or a pharmaceutically active derivative thereof.

3. The method of claim 1 wherein the mammalian subject is a human.

4. A method for treating a protozoal infection in a mammalian subject where the infective agent is resistant to one or more other therapies, comprising the step of administering to the subject a composition comprising an effective anti-protozoal amount of a compound of claim 1.

5. A method as defined in claim 1, wherein the protozoal infection is an infection caused by *Trypanosoma*.

6. A method as defined in claim 1, wherein the protozoal infection is an infection caused by *Leishmania*.

* * * * *